United States Patent
Zaniboni et al.

(10) Patent No.: US 10,814,056 B2
(45) Date of Patent: Oct. 27, 2020

(54) ELASTIC PROTECTION TUBE FOR A HOLLOW FIBER BLOOD PROCESSING APPARATUS

(71) Applicant: Sorin Group Italia S.r.l., Milan (IT)

(72) Inventors: Andrea Zaniboni, S. Martino S. Mirandola (IT); Sara Menozzi, Campogalliano (IT); Francesco Benatti, Concordia sulla Secchia (IT)

(73) Assignee: Sorin Group Italia S.r.l., Milan (IT)

( * ) Notice: Subject to any disclaimer, the term of this patent is extended or adjusted under 35 U.S.C. 154(b) by 784 days.

(21) Appl. No.: 15/525,853

(22) PCT Filed: Nov. 12, 2014

(86) PCT No.: PCT/IB2014/065987
§ 371 (c)(1),
(2) Date: May 10, 2017

(87) PCT Pub. No.: WO2016/075514
PCT Pub. Date: May 19, 2016

(65) Prior Publication Data
US 2017/0319767 A1      Nov. 9, 2017

(51) Int. Cl.
*A61M 1/16*     (2006.01)
*B01D 53/22*    (2006.01)
*B01D 63/02*    (2006.01)

(52) U.S. Cl.
CPC ........... *A61M 1/1698* (2013.01); *B01D 53/22* (2013.01); *B01D 63/02* (2013.01); *B01D 2313/23* (2013.01); *B01D 2313/56* (2013.01)

(58) Field of Classification Search
CPC ............. A61M 1/1698; A61M 1/1678; A61M 1/3627; A61M 1/3638; B01D 53/11; B01D 63/02; B01D 2313/23; B01D 2313/56
See application file for complete search history.

(56) References Cited

U.S. PATENT DOCUMENTS 3,339,341 A * 9/1967 Murdock ............. B01D 63/021
                                                        95/53
3,957,648 A   5/1976 Roget et al.
(Continued)

FOREIGN PATENT DOCUMENTS

CN     1042082 A     5/1990
CN     2511309 Y     9/2002
(Continued)

OTHER PUBLICATIONS

European Search Report issued in EP Application No. 10161451, dated Sep. 28, 2010, 5 pages.
(Continued)

*Primary Examiner* — Philip R Wiest
(74) *Attorney, Agent, or Firm* — Seager, Tufte & Wickhem LLP.

(57) ABSTRACT

A blood processing apparatus includes a housing, a shell, a fiber bundle, and an elastic tube. The housing has a blood inlet and a blood outlet and the shell is situated in the housing and configured to receive blood through the blood inlet. The shell includes a surface and one or more apertures extending through the surface to permit the blood to flow to an exterior of the shell. The fiber bundle includes gas exchanger hollow fibers situated about the shell such that gas flows through and the blood flows across the gas exchanger hollow fibers. The elastic tube includes a fiber web situated about the fiber bundle and configured to elastically constrain and protect the gas exchanger hollow fibers during the insertion into the housing. The fiber web has a pore size that permits the blood to flow across the fiber web without filtering micro-emboli from the blood.

23 Claims, 13 Drawing Sheets

(56) References Cited

U.S. PATENT DOCUMENTS

| | | |
|---|---|---|
| 4,038,190 A | 7/1977 | Baudet et al. |
| 4,225,439 A | 9/1980 | Spranger |
| 4,229,305 A | 10/1980 | Fecondini et al. |
| 4,597,868 A | 7/1986 | Watanabe |
| 4,639,353 A | 1/1987 | Takemura et al. |
| 4,707,268 A | 11/1987 | Shah et al. |
| 4,758,341 A | 7/1988 | Banner |
| 4,902,476 A | 2/1990 | Gordon et al. |
| 5,169,530 A | 12/1992 | Schucker et al. |
| 5,192,439 A | 3/1993 | Roth et al. |
| 5,192,499 A | 3/1993 | Sakai et al. |
| 5,270,004 A | 12/1993 | Cosentino et al. |
| 5,316,724 A | 5/1994 | Mathewson et al. |
| 5,338,512 A | 8/1994 | Mathewson et al. |
| 5,514,095 A | 5/1996 | Brightbill et al. |
| 5,578,267 A | 11/1996 | Cosentino et al. |
| 5,651,765 A | 7/1997 | Haworth et al. |
| 5,674,452 A | 10/1997 | Carson et al. |
| 5,733,398 A | 3/1998 | Carson et al. |
| 5,762,868 A | 6/1998 | Leonard |
| 5,762,869 A | 6/1998 | White et al. |
| 5,817,278 A | 10/1998 | Fini et al. |
| 5,817,279 A | 10/1998 | Eilers et al. |
| 5,830,370 A | 11/1998 | Maloney, Jr. et al. |
| RE36,774 E | 7/2000 | Cosentino et al. |
| 6,105,664 A | 8/2000 | Gillbrand et al. |
| 6,113,782 A | 9/2000 | Leonard |
| 6,241,945 B1 | 6/2001 | Owen |
| 6,454,999 B1 | 9/2002 | Farhangia et al. |
| 6,459,937 B1 | 10/2002 | Morgan et al. |
| 6,755,894 B2 | 6/2004 | Bikson et al. |
| 6,960,322 B2 | 11/2005 | Stringer et al. |
| 7,431,754 B2 | 10/2008 | Ogihara et al. |
| 7,947,113 B2 | 5/2011 | Ogihara et al. |
| 7,981,121 B2 | 7/2011 | Stegfeldt et al. |
| 8,142,546 B2 | 3/2012 | Ogihara et al. |
| 8,318,092 B2 | 11/2012 | Reggiani et al. |
| 8,388,566 B2 | 3/2013 | Reggiani et al. |
| 8,394,049 B2 | 3/2013 | Reggiani et al. |
| 8,425,838 B2 | 4/2013 | Mizoguchi et al. |
| 8,652,406 B2 | 2/2014 | Reggiani et al. |
| 8,685,319 B2 | 4/2014 | Olson et al. |
| 8,795,220 B2 | 8/2014 | Reggiani et al. |
| 8,865,067 B2 | 10/2014 | Olson et al. |
| 8,911,666 B2 | 12/2014 | Mizoguchi et al. |
| 8,980,176 B2 | 3/2015 | Reggiani et al. |
| 9,162,022 B2 | 10/2015 | Reggiani et al. |
| 9,402,943 B2 | 8/2016 | Reggiani et al. |
| 9,566,376 B2* | 2/2017 | Kashefi Khorasani ............ B01D 63/02 |
| 10,098,994 B2 | 10/2018 | Silvestri et al. |
| 10,159,777 B2 | 12/2018 | Reggiani et al. |
| 10,322,223 B2* | 6/2019 | Ochel ................ B01D 19/0031 |
| 10,369,262 B2 | 8/2019 | Reggiani |
| 2002/0039543 A1 | 4/2002 | Ikeda et al. |
| 2002/0049401 A1 | 4/2002 | Ghelli et al. |
| 2003/0080047 A1 | 5/2003 | Watkins et al. |
| 2003/0175149 A1 | 9/2003 | Searles et al. |
| 2004/0149645 A1 | 8/2004 | Sunohara et al. |
| 2004/0175292 A1 | 9/2004 | Ghellil et al. |
| 2004/0251011 A1 | 12/2004 | Kudo |
| 2006/0016743 A1 | 1/2006 | Ogihara et al. |
| 2007/0107884 A1 | 5/2007 | Sirkar et al. |
| 2007/0166190 A1 | 7/2007 | Ogihara et al. |
| 2007/0231203 A1 | 10/2007 | Mizoguchi et al. |
| 2008/0234623 A1 | 9/2008 | Strauss et al. |
| 2010/0106072 A1 | 4/2010 | Kashefi-Khorasani et al. |
| 2010/0269342 A1 | 10/2010 | Carpenter et al. |
| 2010/0272606 A1 | 10/2010 | Carpenter et al. |
| 2010/0272607 A1 | 10/2010 | Carpenter et al. |
| 2011/0268608 A1 | 11/2011 | Reggiani et al. |
| 2011/0268609 A1 | 11/2011 | Reggiani et al. |
| 2012/0046594 A1 | 2/2012 | Reggiani et al. |
| 2012/0121463 A1 | 5/2012 | Reggiani et al. |
| 2012/0294761 A1* | 11/2012 | Reggiani ............ A61M 1/1629 422/46 |
| 2012/0308434 A1* | 12/2012 | Kawamura ......... A61M 1/1698 422/46 |
| 2013/0142695 A1 | 6/2013 | Reggiani et al. |
| 2013/0142696 A1 | 6/2013 | Reggiani et al. |
| 2014/0030146 A1 | 1/2014 | Takeuchi |
| 2014/0154137 A1* | 6/2014 | Kashefi Khorasani ...................... A61M 1/1698 422/46 |
| 2014/0227133 A1 | 8/2014 | Reggiani et al. |
| 2015/0068670 A1 | 3/2015 | Mizoguchi et al. |
| 2016/0325036 A1 | 11/2016 | Silvestri et al. |
| 2016/0354529 A1 | 12/2016 | Reggiani et al. |
| 2017/0072123 A1 | 3/2017 | Reggiani |
| 2018/0133388 A1 | 5/2018 | Mazzoli et al. |
| 2019/0091395 A1 | 3/2019 | Reggiani et al. |
| 2019/0290821 A1 | 9/2019 | Reggiano |

FOREIGN PATENT DOCUMENTS

| | | |
|---|---|---|
| CN | 1308549 C | 9/2005 |
| CN | 2772515 Y | 4/2006 |
| CN | 1907508 A | 2/2007 |
| CN | 1914474 A | 2/2007 |
| CN | 201510571 U | 6/2010 |
| CN | 101837151 A | 9/2010 |
| CN | 201978219 U | 9/2011 |
| CN | 103180032 A | 6/2013 |
| CN | 103328019 A | 9/2013 |
| CN | 103547298 A | 1/2014 |
| CN | 106029118 A | 10/2016 |
| DE | 19782098 T1 | 11/1999 |
| DE | 102007010112 A1 | 9/2008 |
| DE | 102010027973 A1 | 10/2011 |
| EP | 0170210 B1 | 2/1986 |
| EP | 0312125 A1 | 4/1989 |
| EP | 0582959 A1 | 2/1994 |
| EP | 0895786 A1 | 2/1999 |
| EP | 1108462 A2 | 6/2001 |
| EP | 1180374 A1 | 2/2002 |
| EP | 1371381 A1 | 12/2003 |
| EP | 1618906 B1 | 1/2006 |
| EP | 1834656 B1 | 9/2007 |
| EP | 2420262 B1 | 2/2012 |
| EP | 2524712 A1 | 11/2012 |
| EP | 2537543 A1 | 12/2012 |
| JP | 445526 B | 3/1969 |
| JP | S52126681 A | 10/1977 |
| JP | S59147603 A | 8/1984 |
| JP | 60053156 A | 3/1985 |
| JP | S6178407 A | 4/1986 |
| JP | S63139562 A | 6/1988 |
| JP | S63283709 A | 11/1988 |
| JP | 03169329 A | 7/1991 |
| JP | H042067 B2 | 1/1992 |
| JP | 04-039862 B2 | 6/1992 |
| JP | H0439862 B2 | 6/1992 |
| JP | H05177117 A | 7/1993 |
| JP | H0788178 A | 4/1995 |
| JP | H08168525 A | 7/1996 |
| JP | H11508476 A | 7/1999 |
| JP | 2000501954 A | 2/2000 |
| JP | 2000093510 A | 4/2000 |
| JP | 3228518 B2 | 11/2001 |
| JP | 2002506692 A | 3/2002 |
| JP | 3284568 B2 | 5/2002 |
| JP | 2002306592 A | 10/2002 |
| JP | 2003520617 A | 7/2003 |
| JP | 2003525736 A | 9/2003 |
| JP | 2004216143 A | 8/2004 |
| JP | 2006034466 A | 2/2006 |
| JP | 2007190218 A | 7/2007 |
| JP | 2007244880 A | 9/2007 |
| JP | 3992377 B2 | 10/2007 |
| JP | 2007260151 A | 10/2007 |
| JP | 2007328114 A | 12/2007 |
| JP | 2009-093659 A | 4/2009 |

(56) References Cited

FOREIGN PATENT DOCUMENTS

| | | | |
|---|---|---|---|
| JP | 201147269 A | 3/2011 | |
| JP | 5020111 B2 | 9/2012 | |
| JP | 2012239885 A | 12/2012 | |
| JP | 201363121 A | 4/2013 | |
| JP | 2015144857 A | 8/2015 | |
| JP | 2017-510340 A | 4/2017 | |
| WO | WO1997016213 A2 | 5/1997 | |
| WO | WO1997019714 A1 | 6/1997 | |
| WO | WO1997033636 A1 | 9/1997 | |
| WO | WO9947189 A1 | 9/1999 | |
| WO | WO9958171 A2 | 11/1999 | |
| WO | WO2010124087 A1 | 10/2010 | |
| WO | 2012066439 A1 | 5/2012 | |
| WO | 2012133372 A1 | 10/2012 | |
| WO | 2015104725 A1 | 7/2015 | |
| WO | 2015107486 A2 | 7/2015 | |
| WO | 2015128886 A1 | 9/2015 | |

OTHER PUBLICATIONS

European Search Report issued in EP Application No. 10173436, dated Feb. 14, 2011, 7 pages.
European Search Report issued in EP Application No. 10186550, dated Jan. 27, 2011, 7 pages.
European Search Report issued in EP Application No. 10191140, dated Nov. 30, 2011, 8 pages.
European Search Report issued in EP Application No. 12187501, dated Nov. 20, 2013, 6 pages.
European Search Report issued in EP Application No. 13161841, dated Jun. 11, 2013, 6 pages.
International Preliminary Report on Patentability issued in PCT/IB2014/065987, dated May 26, 2017, 9 pages.
International Preliminary Report on Patentability issued in PCT/IT2014/000005, dated Jul. 12, 2016, 6 pages.
International Preliminary Report on Patentability issued in PCT/IT2014/000058, dated Sep. 6, 2016, 10 pages.
International Search Report and Written Opinion issued in PCT/IB2012/052424, dated Oct. 24, 2012, 17 pages.
International Search Report and Written Opinion issued in PCT/IB2014/065987, dated Jul. 6, 2015, 10 pages.
International Search Report and Written Opinion issued in PCT/IT2014/000005, dated Sep. 26, 2014, 9 pages.
International Search Report and Written Opinion issued in PCT/IT2014/000058, dated Dec. 8, 2014, 14 pages.
International Search Report issued in PCT/IB2011/054725, dated Feb. 9, 2012, 12 pages.
Italian Search Report issued in IT Application No. IT MO20140010, completed Sep. 23, 2014, 7 pages.
International Preliminary Report on Patentability issued in PCT/IB2014/065987, dated May 16, 2017, 8 pages.
International Preliminary Report on Patentability issued in PCT/IB2015/053493, dated Nov. 23, 2017, 9 pages.
International Search Report and Written Opinion issued in PCT/IB2015/053493, dated Jan. 18, 2016, 13 pages.
International Preliminary Report on Patentability received for PCT Patent Application No. PCT/IB2012/052424, dated Nov. 28, 2013, 11 pages.
International Search Report and Written Opinion received for PCT Patent Application No. PCT/IT2014/000005, dated Sep. 26, 2014, 8 pages.

* cited by examiner

ELASTIC PROTECTION TUBE FOR A HOLLOW FIBER BLOOD PROCESSING APPARATUS

CROSS-REFERENCE TO RELATED APPLICATION

This application is a national stage application of PCT/IB2014/065987, filed Nov. 12, 2014, which is herein incorporated by reference in its entirety.

TECHNICAL FIELD

This disclosure relates to blood processing systems and more particularly to blood processing systems that are used in blood perfusion systems.

BACKGROUND

Blood perfusion entails encouraging blood through the blood vessels of the body. Typically, blood perfusion systems include one or more pumps in an extracorporeal circuit that is interconnected with the vascular system of a patient. In cardiopulmonary bypass surgery, a blood perfusion system provides for the temporary cessation of the heart beating to create an unmoving operating field by replacing the function of the heart and lungs. Such isolation allows for the surgical correction of medical problems including vascular stenosis, valve disorders, and congenital heart defects. Blood perfusion systems used in cardiopulmonary bypass surgery have an extracorporeal blood circuit that includes at least one pump and an oxygenation device to replace the functions of the heart and lungs.

In cardiopulmonary bypass procedures, oxygen-poor blood, i.e., venous blood, is gravity-drained or vacuum suctioned from a large vein entering the heart right atrium or other veins in the body, such as the femoral vein. The oxygen-poor blood is transferred through a venous line in the extracorporeal circuit and pumped to an oxygenator that provides for oxygen transfer to the blood. The oxygen can be introduced into the blood by transfer across a microporous membrane or, less frequently, by bubbling oxygen through the blood. Concurrently, carbon dioxide is removed across the membrane. The oxygenated blood is then returned through an arterial line to the aorta, femoral artery, or another artery.

Surgeons and patients would welcome advances in blood processing systems that are used in blood perfusion systems.

SUMMARY

In some embodiments described in the disclosure, a blood processing apparatus includes a housing, a shell, a fiber bundle, and an elastic tube. The housing has a blood inlet and a blood outlet and the shell is situated in the housing and configured to receive blood through the blood inlet. The shell includes a surface and one or more apertures extending through the surface to permit the blood to flow to an exterior of the shell. The fiber bundle includes gas exchanger hollow fibers situated about the shell such that gas flows through the gas exchanger hollow fibers and the blood flows across the gas exchanger hollow fibers. The elastic tube includes a fiber web situated about the fiber bundle and configured to elastically constrain and protect the gas exchanger hollow fibers, wherein the fiber web has a pore size such that the fiber web permits the blood to flow across the fiber web without filtering micro-emboli from the blood.

In some embodiments described in the disclosure, a blood processing apparatus includes a housing, a heat exchanger, a shell, a fiber bundle, and an elastic tube. The housing has a blood inlet and a blood outlet and the heat exchanger is situated in the housing and configured to receive blood through the blood inlet and regulate the temperature of the blood. The shell is situated about the heat exchanger and includes a surface and one or more apertures extending through the surface to permit the blood to flow to an exterior of the shell. The fiber bundle includes gas exchanger hollow fibers situated about the shell such that gas flows through the gas exchanger hollow fibers and the blood flows across the gas exchanger hollow fibers. The elastic tube has a tube interior and a tube exterior such that the fiber bundle is situated in the tube interior and the tube exterior is situated next to the housing. The elastic tube elastically constrains and protects the gas exchanger hollow fibers as the fiber bundle and the elastic tube are introduced into the housing and maintained in the housing. Also, the elastic tube has an average pore size diameter with a best fit circle of greater than 200 micrometers that permits the blood to flow from the tube interior to the tube exterior without filtering micro-emboli from the blood and with a reduced hydraulic resistance to blood flow.

In some embodiments described in the disclosure, a method of manufacturing a blood processing apparatus includes: providing gas exchanger hollow fibers; winding the gas exchanger hollow fibers onto a shell to provide a fiber bundle on the shell; providing an elastic tube including a fiber web that permits blood to flow across the fiber web without filtering micro-emboli from the blood; introducing the fiber bundle and the shell into the elastic tube; and introducing the elastic tube containing the fiber bundle and the shell into a housing such that the fiber web elastically constrains the gas exchanger hollow fibers and protects the gas exchanger hollow fibers from being mechanically damaged by the housing during the introduction.

In some embodiments described in the disclosure, a method of pre-cleaning an elastic tube used in a blood processing apparatus includes: washing the elastic tube with a solvent; washing the elastic tube with purified water; and sterilizing the elastic tube with steam sterilization.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
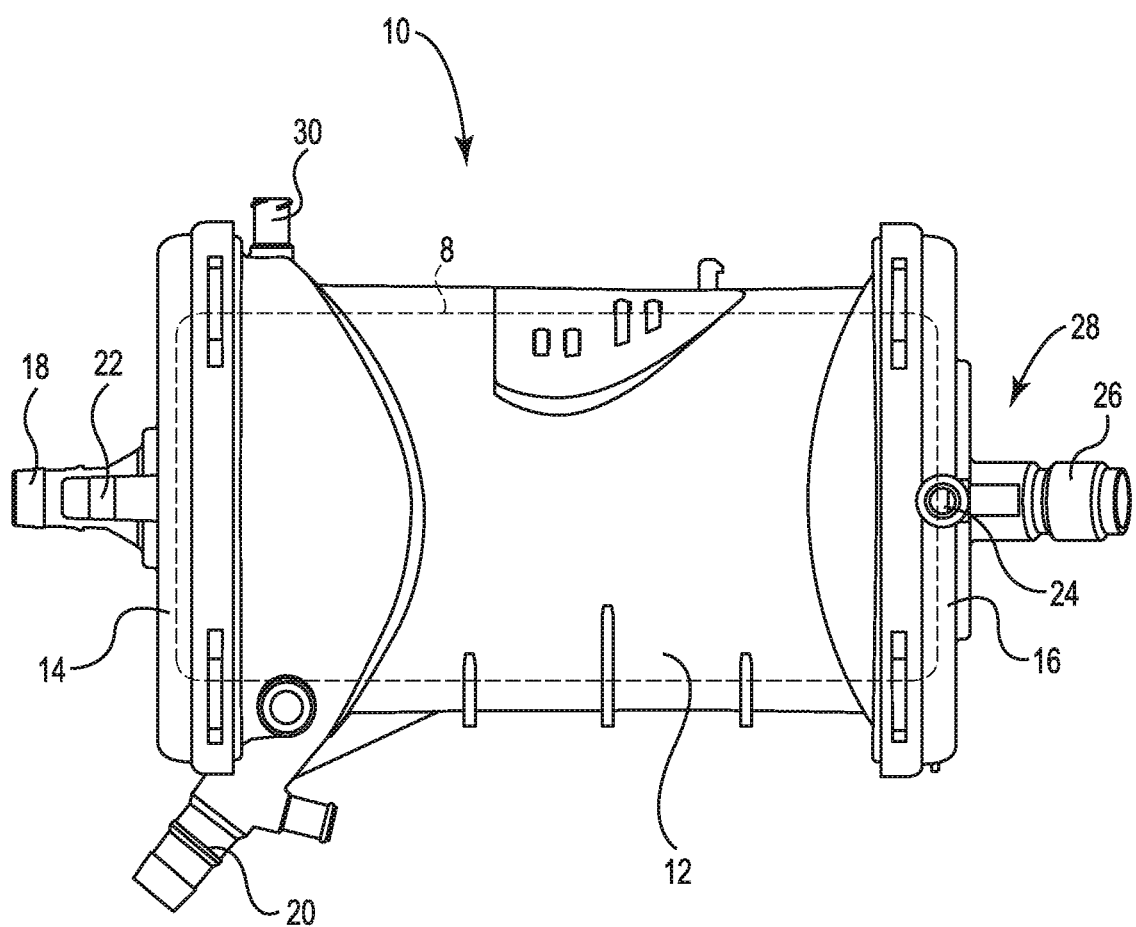
FIG. 1 is a schematic illustration of a blood processing apparatus, in accordance with embodiments described in the disclosure.

Embodiments have been shown by way of example in the drawings and are described in detail below. The intention is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The disclosure describes a blood processing apparatus that, according to some embodiments, includes a heat exchanger and a gas exchanger. The blood processing apparatus can be used in an extracorporeal blood circuit, such as that used in a cardiopulmonary bypass procedure, which includes several different elements, such as a pump, a blood reservoir, and an oxygenator. In some embodiments, the term oxygenator refers to an integrated structure that combines a heat exchanger and a gas exchanger in a unitary device. In some embodiments, the heat exchanger and the gas exchanger are disposed concentrically with one component situated inside the other component. In some embodiments, the heat exchanger and the gas exchanger are structurally distinct structures operably coupled to each other.

The disclosure describes a blood processing apparatus that includes a gas exchanger that includes an elastic tube disposed about a fiber bundle of gas exchanger hollow fibers. The elastic tube is situated about the fiber bundle to elastically constrain and protect the gas exchanger hollow fibers.

In some embodiments, the fiber bundle is wrapped around a shell and the elastic tube, the fiber bundle, and the shell are situated in a housing that includes a blood inlet and a blood outlet. The shell receives blood through the blood inlet and includes a surface and at least one aperture extending through the surface to permit the blood to flow to an exterior of the shell and the fiber bundle. Gas flows through the gas exchanger hollow fibers and blood flows across the gas exchanger hollow fibers to oxygenate the blood and remove carbon dioxide from the blood. The elastic tube has a pore size that permits the blood to flow across the elastic tube and out of the blood outlet without filtering micro-emboli from the blood. In some embodiments, the elastic tube/fiber bundle/shell assembly is introduced into the housing as a single unit. In some embodiments, the blood processing apparatus includes a heat exchanger situated in the housing and configured to receive blood and regulate the temperature of the blood.

FIG. 1 is a schematic illustration of a blood processing apparatus or oxygenator 10, in accordance with embodiments described in the disclosure. While some of the internal components of the blood processing apparatus 10 are not visible in this illustration, the blood processing apparatus 10 includes a gas exchanger that includes an elastic tube 8, indicated in dashed lines. The elastic tube 8 is disposed about a fiber bundle that includes gas exchanger hollow fibers that are used to oxygenate the blood and remove carbon dioxide from the blood. The elastic tube 8 is situated about the fiber bundle to elastically constrain and protect the gas exchanger hollow fibers. Also, the elastic tube 8 has a pore size that permits the blood to flow across the elastic tube 8 without filtering micro-emboli from the blood and with a reduced hydraulic resistance to blood flow.

The blood processing apparatus 10 includes a housing 12, a first end cap 14 that is secured to the housing 12, and a second end cap 16 that is secured to the housing 12. The gas exchanger, including the elastic tube 8 and the fiber bundle, is situated in the housing 12. In some embodiments, the blood processing apparatus 10 includes a heat exchanger. In some embodiments, the blood processing apparatus 10 includes a heat exchanger and the heat exchanger and the gas exchanger are integrated into a single structure. In some embodiments, the housing 12 includes other structure that enables attachment of the housing 12 to other devices.

While the housing 12 is illustrated as largely cylindrical in shape, in some embodiments the housing 12 has another shape, such as a cuboid shape, a triangular prism shape, or a hexagonal prism shape. Also, in some embodiments, the gas exchanger has the same shape or a different shape than the housing 12, and in some embodiments, a heat exchanger has the same shape or a different shape than the housing 12. In some embodiments, the blood processing apparatus 10 includes a heat exchanger and a gas exchanger, and the heat exchanger is situated inside of the gas exchanger. In some embodiments, the heat exchanger and the gas exchanger are concentrically aligned with one another.

The housing 12 and the first and second end caps 14 and 16 include a number of inlets and outlets for gas and fluid flow into the housing 12 and out of the housing 12, respectively. For blood flow, a blood inlet 18 extends into the housing 12 and a blood outlet 20 exits the housing 12. For gas flow, a gas inlet 22 extends into the housing 12 and a gas outlet 24 exits the housing 12 and, in embodiments that include a heat exchanger, for heat exchanger fluid, a heat exchanger fluid inlet 26 extends into the housing 12 and a heat exchanger fluid outlet 28, which is behind the heat exchanger fluid inlet 26 in FIG. 1, exits the housing 12. In some embodiments, the heat exchanger fluid inlet 26 is disposed at one end of the housing 12 and the heat exchanger fluid outlet 28 is disposed at an opposite end of the housing 12. In some embodiments, the blood processing apparatus 10 includes a purge port 30 that operates to permit gases, e.g., air bubbles, which exit the blood to be vented or aspirated and removed from the blood processing apparatus 10. In some embodiments, the purge port 30 includes a valve or a threaded cap.

The positions of the inlets 18, 22, and 26, the outlets 20, 24, and 28, and the purge port 30 are merely illustrative, as other arrangements and configurations are contemplated.

Figure 2:
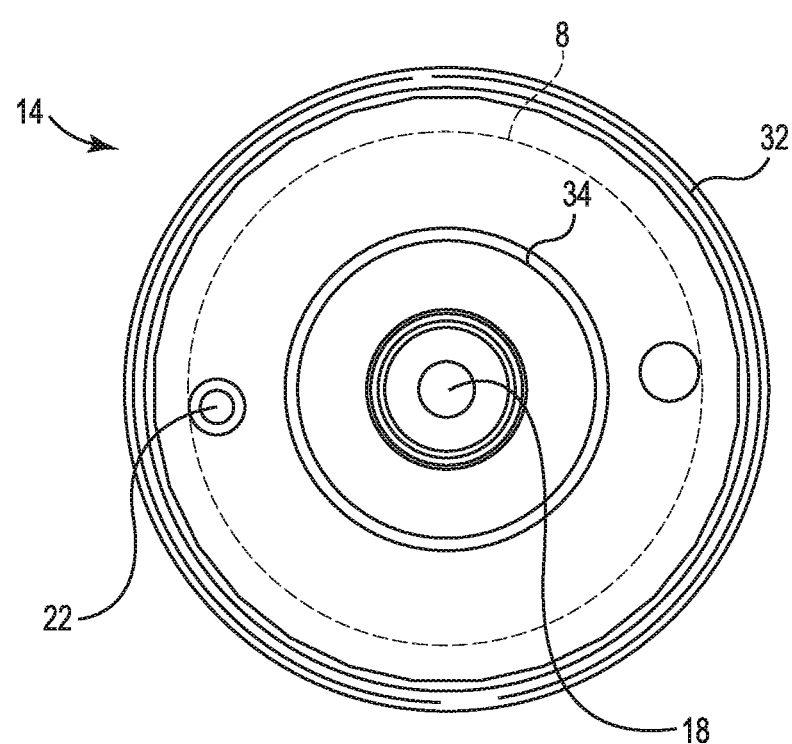
FIG. 2 is an illustration of a first blood inlet end cap, in accordance with embodiments described in the disclosure.
Figure 3:
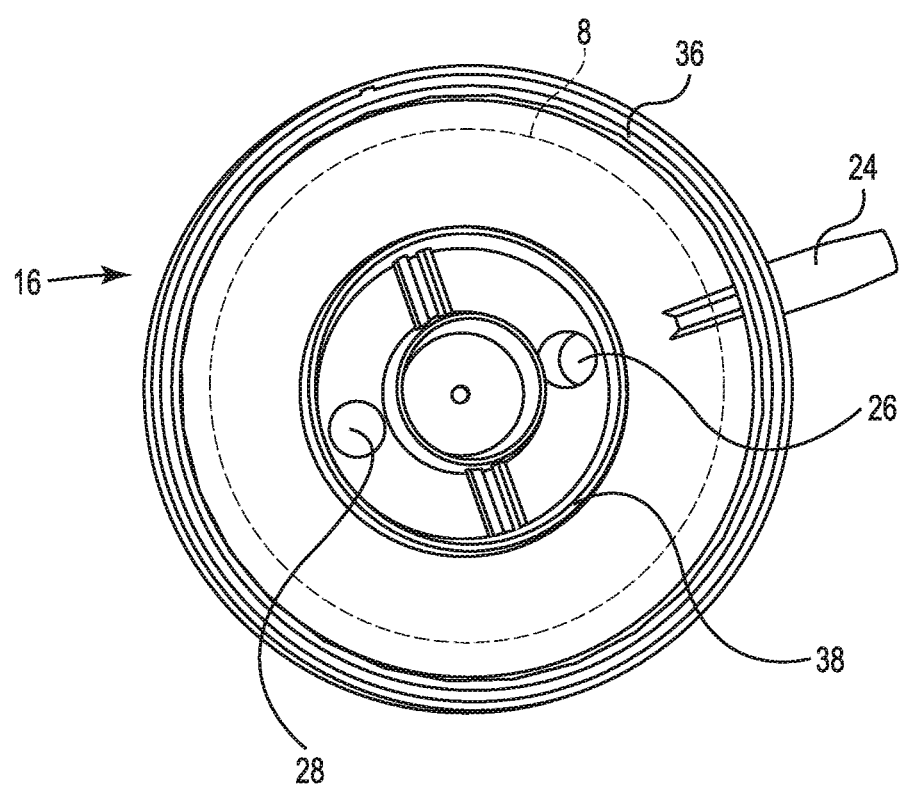
FIG. 3 is an illustration of a second water in/out end cap, in accordance with embodiments described in the disclosure.

FIGS. 2 and 3 illustrate the first end cap 14 and the second end cap 16, respectively, in accordance with embodiments described in the disclosure. The first end cap 14 and the second end cap 16 are each configured to be secured to the housing 12. In some embodiments, the first end cap 14 and/or the second end cap 16 are adhesively secured in place. In some embodiments, the first end cap 14 and/or the second end cap 16 are snap-fit into place or threaded onto their respective ends of the housing 12.

FIG. 2 is an illustration of the first end cap 14, in accordance with embodiments described in the disclosure. While the first end cap 14 is illustrated as a standalone part, i.e., not attached to the housing 12, the position of the outer circumference of the elastic tube 8 in the blood processing apparatus 10 of FIG. 1 is indicated in dashed lines for reference.

In some embodiments, the blood inlet 18 and/or the gas inlet 22 are integrally formed with the first end cap 14. For example, in some embodiments, the first end cap 14 can be injection molded with the blood inlet 18 and/or the gas inlet 22 formed as part of the injection molded part. In some embodiments, the first end cap 14 can be formed having apertures to which the blood inlet 18 and/or the gas inlet 22 are attached.

The first end cap 14 includes an annular ring 32 that is disposed about a periphery of the first end cap 14 and that serves, in some embodiments, as an attachment point for securing the first end cap 14 to the housing 12. In some embodiments, the first end cap 14 also includes an annular ring 34 that locates portions of a heat exchanger.

FIG. 3 is an illustration of the second end cap 16, in accordance with embodiments described in the disclosure. While the second end cap 16 is illustrated as a standalone part, i.e., not attached to the housing 12, the position of the outer circumference of the elastic tube 8 in the blood processing apparatus 10 of FIG. 1 is indicated in dashed lines for reference.

In some embodiments, a heat exchanger fluid inlet 26 and/or a heat exchanger fluid outlet 28 are integrally formed with the second end cap 16. For example, in some embodiments, the second end cap 16 can be injection molded with the heat exchanger fluid inlet 26 and/or the heat exchanger fluid outlet 28 formed as part of the injection molded part. Also, in some embodiments, the second end cap 16 can be injected molded with the gas outlet 24 formed as part of the injection molded part. In some embodiments, the second end cap 16 can be formed having apertures to which one or more of the heat exchanger fluid inlet 26, the heat exchanger fluid outlet 28, and/or the gas outlet 24 are attached.

The second end cap 16 includes an annular ring 36 that is disposed about a periphery of the second end cap 16 and that serves, in some embodiments, as an attachment point for securing the second end cap 16 to the housing 12. In some embodiments, the second end cap 16 also includes an annular ring 38 that locates portions of a heat exchanger.

In some embodiments, one of the heat exchanger fluid inlet 26 and the heat exchanger fluid outlet 28 is located in the first end cap 14 and the other of the heat exchanger fluid inlet 26 and the heat exchanger fluid outlet 28 is located in the second end cap 16. Also, in some embodiments, the heat exchanger fluid inlet 26 and outlet 28 can be located in the first end cap 14.

Figure 4:
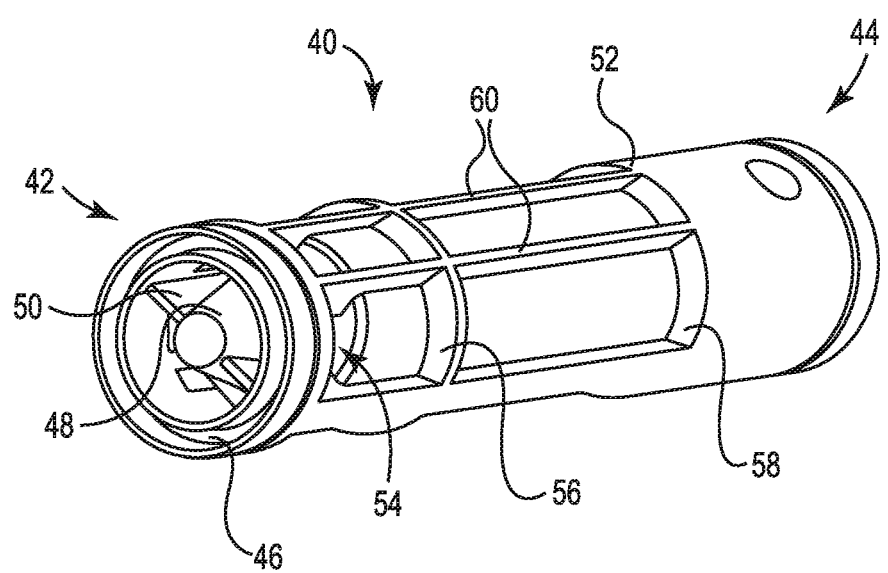
FIG. 4 is a perspective illustration of a heat exchanger core, in accordance with embodiments described in the disclosure.

FIG. 4 is a perspective illustration of a heat exchanger core 40, in accordance with embodiments described in the disclosure. The heat exchanger core 40 has a first end 42 and a second end 44. In some embodiments, the heat exchanger core 40 is disposed within the blood processing apparatus 10 such that the first end 42 is near the first end cap 14 and the second end 44 is near the second end cap 16. The heat exchanger core 40 includes an annular portion 46 that, in some embodiments, helps to locate the first end 42 relative to the first end cap 14. Also, in some embodiments, the second end 44 is configured to help locate the second end 44 relative to the second end cap 16. While the heat exchanger core 40 is illustrated as largely cylindrical in shape, in some embodiments the heat exchanger core 40 has another shape, such as a cuboid shape, a triangular prism shape, or a hexagonal prism shape.

The heat exchanger core 40 includes a conical deflection surface 48 upon which incoming blood, from the blood inlet 18, impinges. The conical deflection surface 48 deflects the blood in a radial direction. In some embodiments, the conical deflection surface 48 includes a divider 50 that assists in directing blood in particular directions.

The heat exchanger core 40 includes an outer surface 52. A core aperture 54 is formed within the outer surface 52, such that blood impinging on the conical deflection surface 48 is deflected radially outwardly through the core aperture 54. In some embodiments, the heat exchanger core 40 has one, two, three, or more core apertures 54 spaced radially about the heat exchanger core 40.

The heat exchanger core 40 includes a first radially disposed core rib 56 and a second radially disposed core rib 58. The core ribs (or projections) 56 and 58 deflect blood away from the outer surface 52 in a radially outward direction and impart a radial component to blood flow trajectory. The heat exchanger core 40 also includes longitudinally extending ribs 60 that serve to promote longitudinal flow paths down the outside of the heat exchanger core 40. In some embodiments, the heat exchanger core 40 includes more than two core ribs 56 and 58. In some embodiments, the ribs 56 and 58 extend circumferentially around or substantially around the outer surface of the heat exchanger core 40.

Figure 5A:
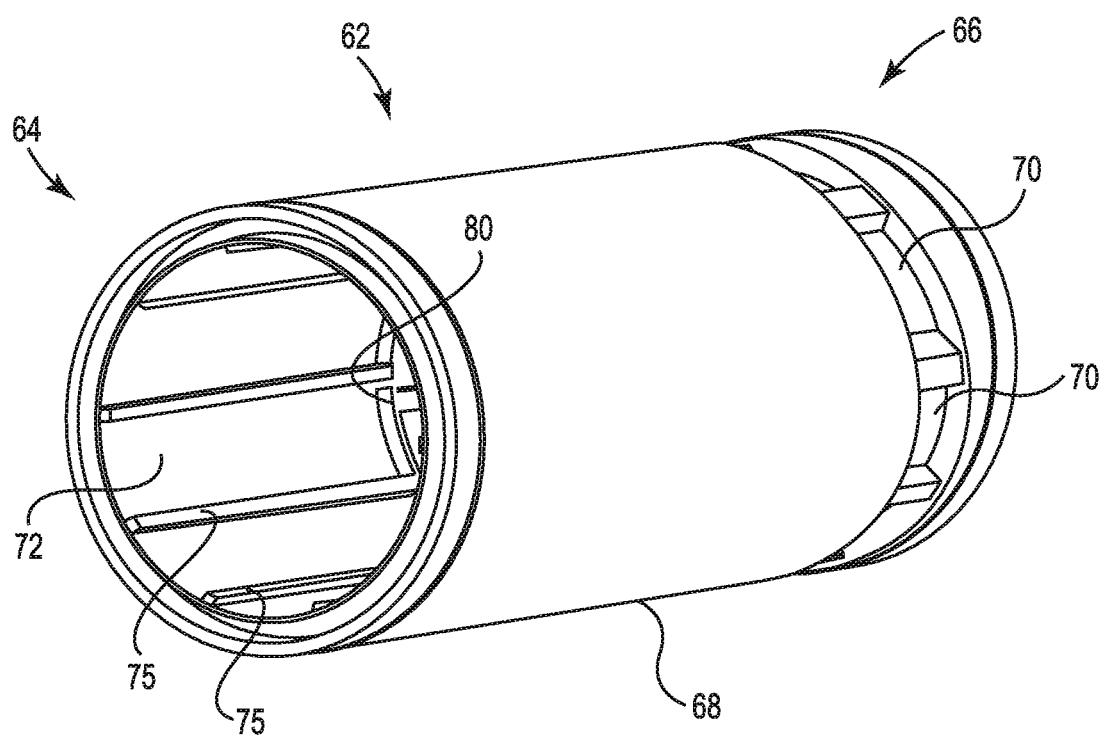
FIG. 5A is a perspective illustration of a cylindrical shell that forms a barrier between a heat exchanger and a gas exchanger, in accordance with embodiments described in the disclosure.
Figure 5B:
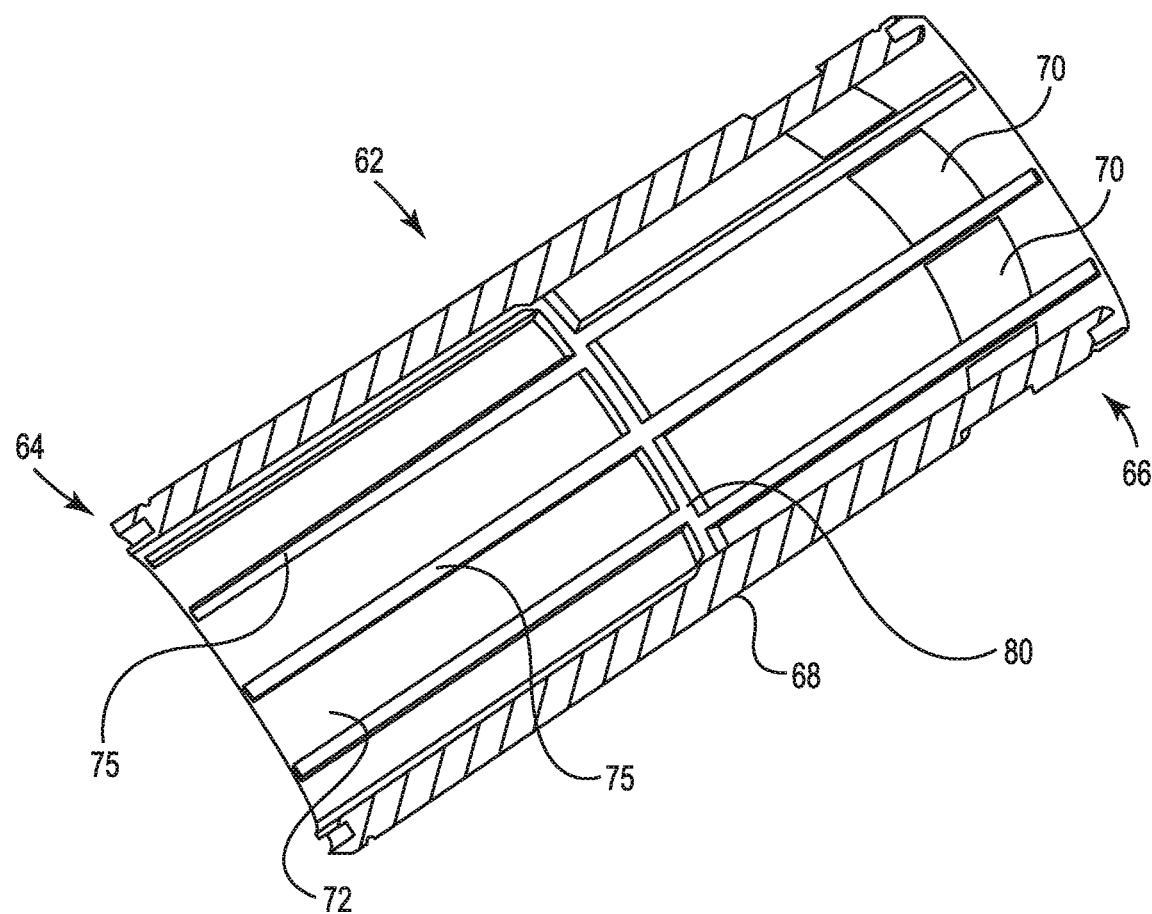
FIG. 5B is a cross-sectional illustration of the cylindrical shell of FIG. 5A, in accordance with embodiments described in the disclosure.
Figure 6:
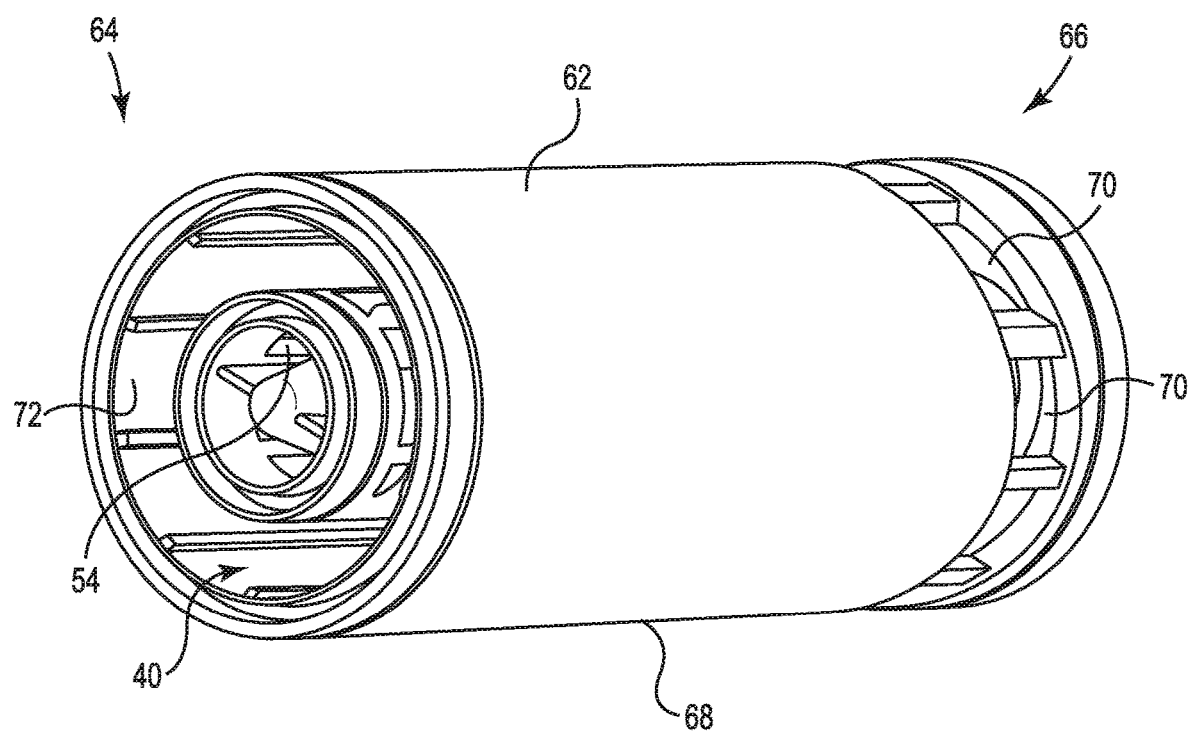
FIG. 6 is a perspective illustration of the heat exchanger core of FIG. 4 disposed within the cylindrical shell of FIGS. 5A and 5B, in accordance with embodiments described in the disclosure.
Figure 7:
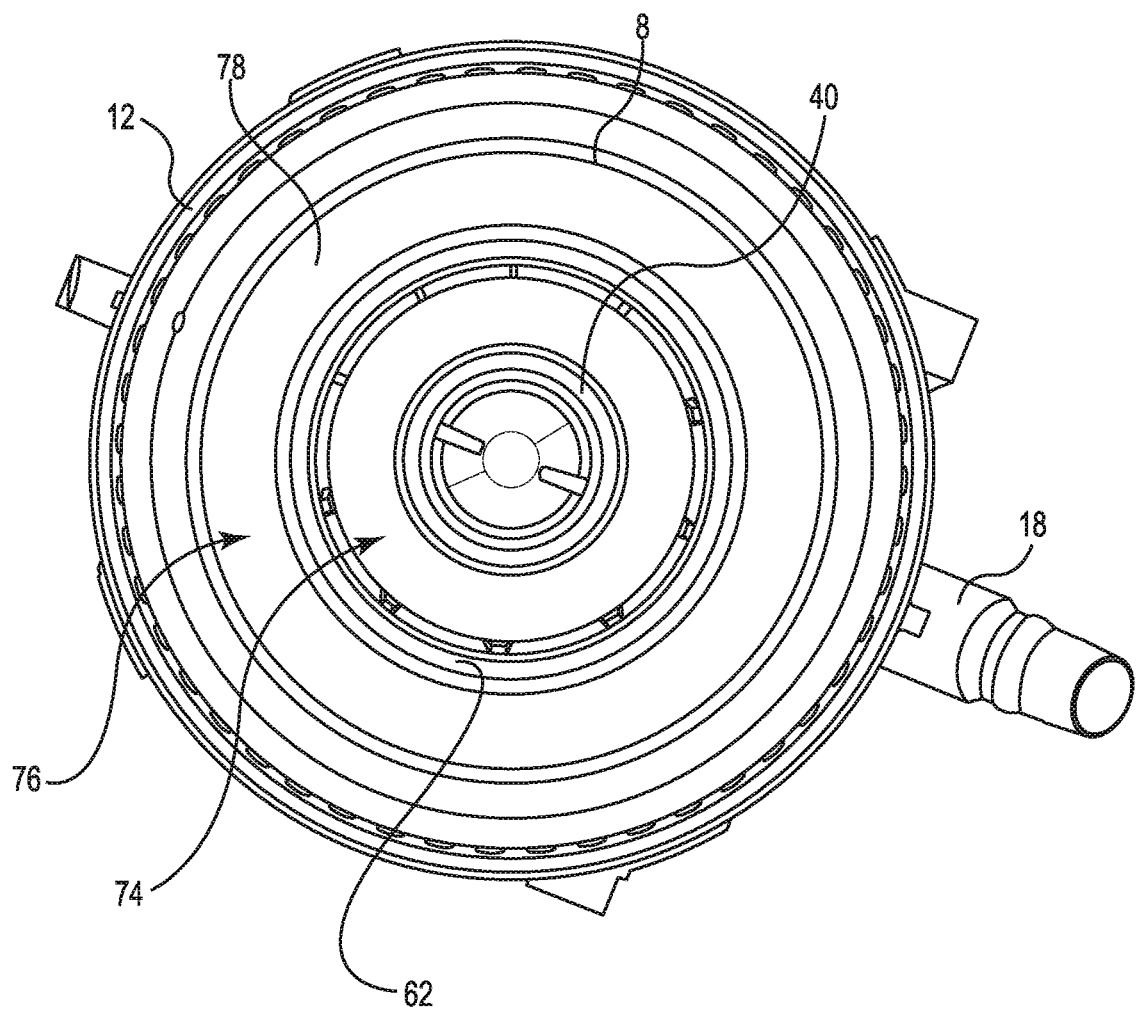
FIG. 7 is a cross-sectional illustration of the blood processing apparatus of FIG. 1, in accordance with embodiments described in the disclosure.

FIG. 5A is a perspective illustration of a cylindrical shell 62 that forms at least a partial barrier between the heat exchanger core 40 and a gas exchanger, in accordance with embodiments described in the disclosure. FIG. 5B is a cross-sectional illustration of the cylindrical shell 62 of FIG. 5A, in accordance with embodiments described in the disclosure. In some embodiments, the heat exchanger core 40 of FIG. 4 is disposed within the cylindrical shell 62 and arranged coaxially with the cylindrical shell 62, as shown in FIG. 6. In some embodiments, the cylindrical shell 62 is disposed within the housing 12 and arranged coaxially with the housing 12, as shown in FIG. 7. While the shell 62 is illustrated as largely cylindrical in shape, in some embodiments the shell 12 has another shape, such as a cuboid shape, a triangular prism shape, or a hexagonal prism shape.

The cylindrical shell 62 includes a first end 64 and a second end 66. In some embodiments, the cylindrical shell 62 is disposed within the housing 12 such that the first end 64 is near the first end cap 14 and the second end 66 is near the second end cap 16.

The cylindrical shell 62 also includes an exterior or outer surface 68. A shell aperture 70 is formed in the outer surface 68 such that blood flowing between the outer surface 52 of the heat exchanger core 40 and an inner surface 72 of the cylindrical shell 62 can exit the cylindrical shell 62 through the shell aperture 70 to the outer surface 68. In some embodiments, the cylindrical shell 62 has one, two, three, four, or more shell apertures 70 spaced radially about the cylindrical shell 62.

In some embodiments, the inner surface 72 of the cylindrical shell 62 includes one or more shell ribs 80 that protrude from the inner surface 72 and extend toward the heat exchanger core 40. These shell ribs 80 deflect blood away from the inner surface 72 in a radially inward direction. In some embodiments, the one or more shell ribs 80, in combination with the core ribs 56 and 58, interrupt longitudinal blood flow and impart a radial flow component to blood flow through the heat exchanger, i.e., between the outer surface 52 of the heat exchanger core 40 and the inner surface 72 of the cylindrical shell 72. In some embodiments, the heat exchanger core 40 includes one or more longitudinally extending ribs 75 that promote longitudinal flow paths between the heat exchanger core 40 and the cylindrical shell 62.

FIG. 6 is a perspective illustration of the heat exchanger core 40 of FIG. 4 disposed within the cylindrical shell 62 of FIG. 5, in accordance with embodiments described in the disclosure. The core aperture(s) 54 and the shell aperture(s) 70 are disposed at opposite ends of the blood processing apparatus 10, such that blood entering the volume between the outer surface 52 of the heat exchanger core 40 and the inner surface 72 of the cylindrical shell 62 is forced to flow substantially the entire length of the blood processing apparatus 10 before exiting the cylindrical shell 62.

FIG. 7 is a cross-sectional illustration of the blood processing apparatus 10 of FIG. 1, in accordance with embodiments described in the disclosure. The blood processing apparatus 10 includes the heat exchanger core 40 of FIG. 4 situated inside the cylindrical shell 62 of FIGS. 5A and 5B. The cylindrical shell 62 is situated inside the housing 12. Also, the heat exchanger core 40 is coaxially aligned with the cylindrical shell 62, which is coaxially aligned with the housing 12.

The blood processing apparatus 10 includes a heat exchanger element 74 disposed between the heat exchanger core 40 and the cylindrical shell 62. Also, the blood processing apparatus 10 includes a gas exchanger element 76 disposed between the cylindrical shell 62 and the housing 12. The elastic tube 8 is disposed about the gas exchanger element 76.

In some embodiments, the heat exchanger element 74 includes a number of hollow fibers through which a heating fluid, such as water, can flow. The blood flows around and past the hollow fibers to regulate the temperature of the blood. In some embodiments, the hollow fibers are polymeric. In some embodiments, the hollow fibers are metallic fibers. In some embodiments, the hollow fibers can be formed of polyurethane, polyester, or other suitable polymer or plastic material. In some embodiments, the hollow fibers have an outer diameter of between 0.2 and 1.0 millimeters, and in some embodiments, the hollow fibers have an outer diameter of between 0.25 and 0.5 millimeters.

The heat exchanger hollow fibers can be woven into mats that can range, for example, from 80 to 200 millimeters in width. In some embodiments, the mats are arranged in a criss-cross configuration. In some embodiments, the mats may be arranged parallel to each other. In other embodiments, the heat exchanger element 74 can include a metal bellows or other structure having a substantial surface area, e.g., fins, for facilitating heat transfer with the blood.

The gas exchanger element 76 includes a number of micro-porous hollow fibers through which a gas, such as oxygen, can flow. The micro-porous hollow fibers are situated on and about the outer surface 68 of the cylindrical shell 62 to provide a fiber bundle 78 on the cylindrical shell 62. The blood flows around and past the micro-porous hollow fibers and, due to concentration gradients, oxygen diffuses through the hollow fibers and into the blood and carbon dioxide diffuses out of the blood and into the hollow fibers. In some embodiments, the micro-porous hollow fibers are wound around the cylindrical shell 62 to provide the fiber bundle 78 on the outer surface 68 of the cylindrical shell 62. In some embodiments, the micro-porous hollow fibers are woven into fiber mats that are wound around the cylindrical shell 62 to provide the fiber bundle 78 on the outer surface 68 of the cylindrical shell 62. In some embodiments, the micro-porous hollow fibers are woven into fiber mats that can range, for example, from 80 to 200 millimeters in width. In some embodiments, the fiber mats are woven in a criss-cross configuration.

In some embodiments, the micro-porous hollow fibers are made of polymethylpentene (PMP), a plasma breakthrough resistant material. In some embodiments, the micro-porous hollow fibers are made of other plasma breakthrough resistant materials. In some embodiments, the micro-porous hollow fibers have an outer diameter of about 0.38 millimeters. In some embodiments, the micro-porous hollow fibers have an outer diameter of between 0.2 and 1.0 millimeters, and in some embodiments, the micro-porous hollow fibers have an outer diameter of between 0.25 and 0.5 millimeters. In other embodiments, the micro-porous hollow fibers are made of polypropylene, polyester, or another suitable polymer or plastic material.

The elastic tube 8 is disposed about the gas exchanger element 76 to elastically constrain and protect the micro-porous hollow fibers of the fiber bundle 78. The elastic tube 8 has a pore size that is large enough to permit blood to flow across the elastic tube 8 without filtering micro-emboli from the blood and to provide a reduced hydraulic resistance to blood flow.

In some embodiments, the elastic tube 8 is situated about the fiber bundle 78 prior to insertion of an assembly, including the elastic tube 8, the fiber bundle 78, and the cylindrical shell 62, into the housing 12 of the blood processing apparatus 10. The elastic tube 8 elastically confines or constrains the micro-porous hollow fibers of the fiber bundle 78 and the elastic tube 8 protects the micro-porous hollow fibers of the fiber bundle 78 from being damaged as the assembly is introduced into the housing 12. This prevents subsequent leaks through the micro-porous hollow fibers. The elastic tube 8 is not removed from the blood processing apparatus 10, such that the elastic tube 8 remains in the housing 12 during storage and operation of the blood processing apparatus 10.

Figure 8:
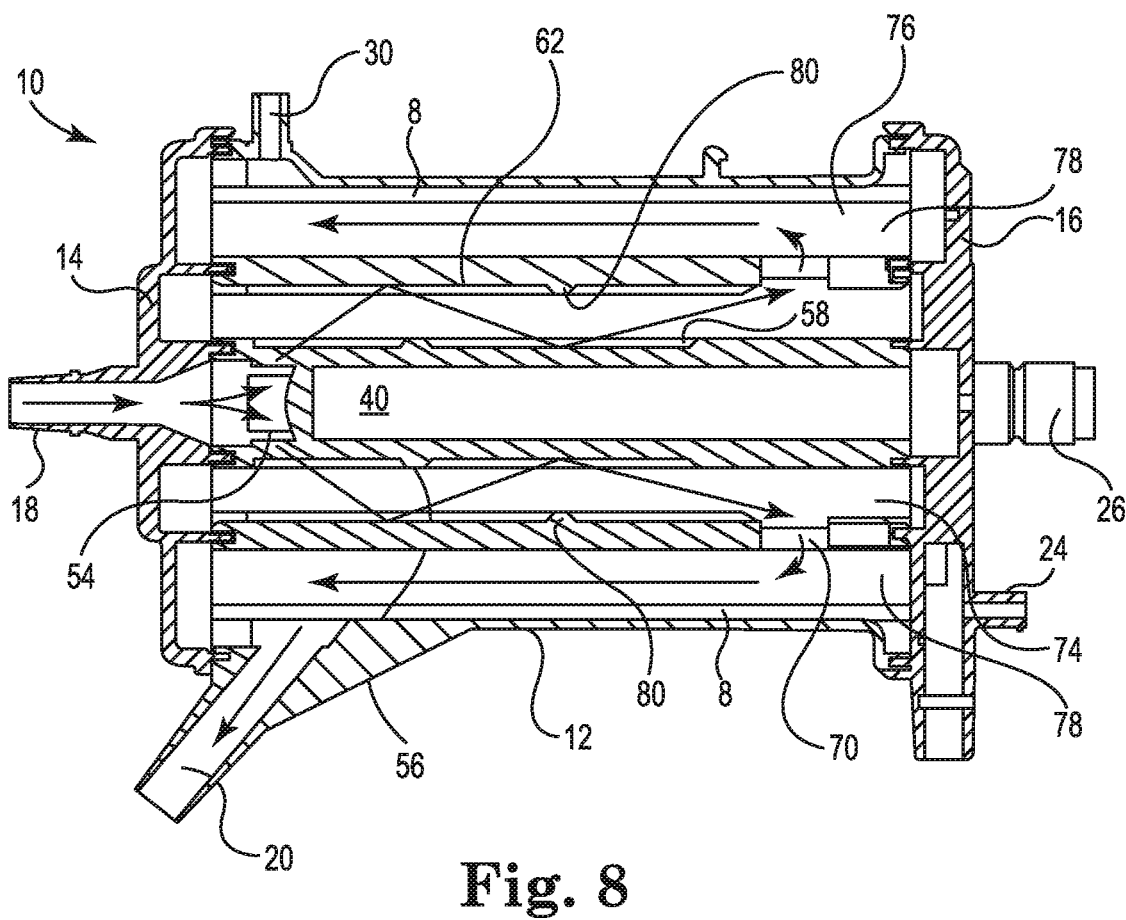
FIG. 8 is a longitudinal cross-sectional illustration of the blood processing apparatus of FIG. 1, in accordance with embodiments described in the disclosure.

FIG. 8 is a longitudinal cross-sectional illustration of the blood processing apparatus 10 of FIG. 1, in accordance with embodiments described in the disclosure. The heat exchanger core 40 is centrally located, with the heat exchanger element 74 coaxially disposed about the heat exchanger core 40. The cylindrical shell 62 is coaxially disposed about the heat exchanger element 74. The gas exchanger element 76 is coaxially disposed about the cylindrical shell 62 to provide the fiber bundle 78 about the outer surface 68 of the cylindrical shell 62. The elastic tube 8 is disposed about the fiber bundle 78, and the housing 12 is coaxially disposed about the elastic tube 8 and the other components. In some embodiments, the heat exchanger core 40 has core ribs 56 and 58 that impart a radial component to blood flow trajectory across the heat exchanger element 74. In some embodiments, the cylindrical shell 62 has radially disposed shell ribs 80 that are configured to impart a radial component to blood flow trajectory across the heat exchanger element 74.

In operation, blood enters the blood processing apparatus 10 through the blood inlet 18 and is radially directed through the core aperture(s) 54, such that the blood flows over and around the hollow fibers within the heat exchanger element 74. At least some of the blood flow impinges on the inner surface 72 of the cylindrical shell 62 and is radially directed back towards the outer surface 52 of the heat exchanger core 40, and at least some of the blood flow is directed radially outwards by the core ribs 56 and 58. The blood continues traveling back and forth radially until it reaches the shell aperture(s) 70. The blood flows through the shell aperture(s) 70 and over and around the micro-porous hollow fibers of the fiber bundle 78 in the space between the cylindrical shell 62 and the housing 12. The blood also flows through the elastic tube 8, which has a pore size that is large enough to permit the blood to flow across the elastic tube 8 without filtering micro-emboli from the blood and with a reduced hydraulic resistance to blood flow. The blood exits the blood processing apparatus 10 through the blood outlet 20.

Figure 9:
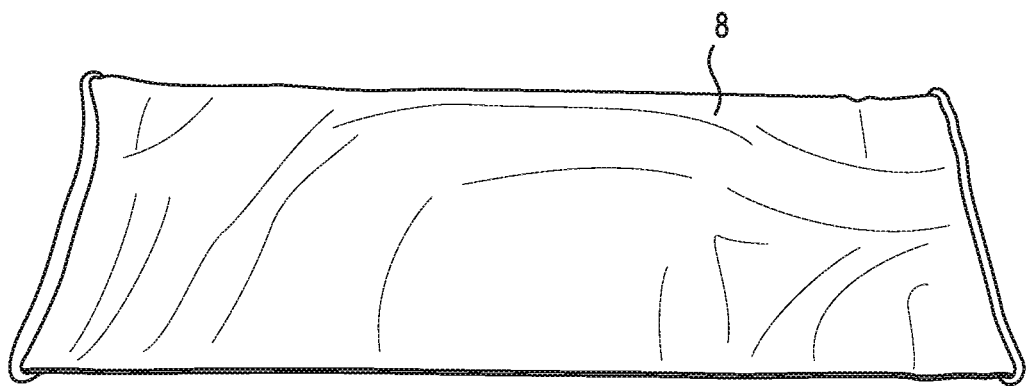
FIG. 9 is an illustration of the elastic tube in an unexpanded, relaxed condition, prior to being disposed on the fiber bundle of the blood processing apparatus, in accordance with embodiments described in the disclosure.

FIG. 9 is an illustration of the elastic tube 8 in a flattened, relaxed condition, prior to being disposed on the fiber bundle 78 of the blood processing apparatus 10, in accordance with embodiments described in the disclosure.

The elastic tube 8 is made from an elastomeric yarn that elastically expands to be disposed about the fiber bundle 78. In some embodiments, the elastomeric yarn includes an inner core of a polyurethane elastic fiber covered with a nylon yarn. In some embodiments, the elastomeric yarn includes an inner core of spandex or elastane covered with a nylon yarn. In some embodiments, a coating is applied to the elastomeric yarn to decrease the contact angle of the surfaces and improve the wettability of the elastic tube 8.

The elastic tube 8 is produced by knitting the elastomeric yarn into the shape of a tube or sock. In some embodiments, the elastic tube 8 is knit on a circular machine, similar to a circular machine that produces socks. In some embodiments, the elastic tube 8 can be weaved into the shape of a tube or sock.

Figure 10:
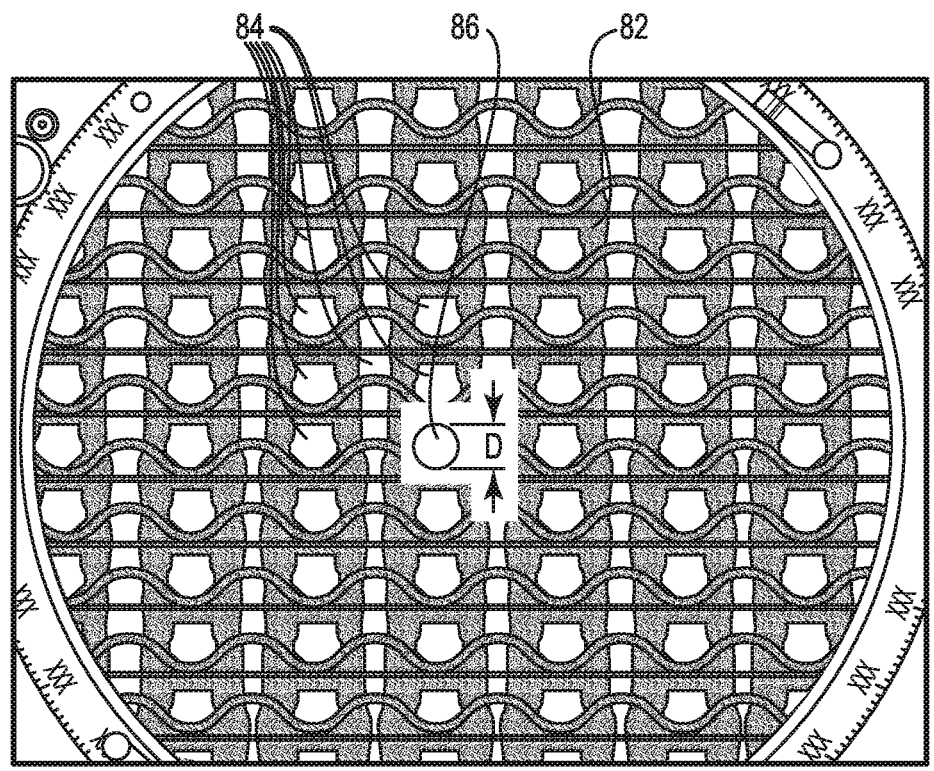
FIG. 10 is a microscopic enlarged illustration of a portion of the elastic tube, in accordance with embodiments described in the disclosure.

FIG. 10 is a microscopic enlarged illustration of a portion of the elastic tube 8, in accordance with embodiments described in the disclosure. The elastic tube 8 includes a fiber web 82 having pores 84 through which blood can flow. The size of the pores 84, referred to as the pore size, is measured by applying a best fit circle, such as circle 86, to the pores 84 of the elastic tube 8. The diameter D of the best fit circles are a measure of the pore sizes.

The elastic tube 8 is made to provide a pore size that permits the blood to flow across the fiber web without filtering micro-emboli from the blood and to reduce the hydraulic resistance of blood flow across the elastic tube 8 through the pores 84. The micro-emboli, including blood clots and bubbles, as measured by a best fit circle technique, have diameters of less than 120 micrometers. The elastic tube 8 is made to provide no significant filtering of solid or gaseous micro-emboli of less than 120 micrometers in diameter of a best fit circle.

In some embodiments, the pores 84 have an average pore size diameter with a best fit circle of 350 micrometers. In some embodiments, the pores 84 have an average pore size diameter with a best fit circle in a range of from 200 to 500 micrometers. In some embodiments, the pores 84 have an average pore size diameter with a best fit circle in a range of from 150 to 800 micrometers. In some embodiments, the pores 84 have an average pore size diameter with a best fit circle of greater than 200 micrometers.

Figure 11:
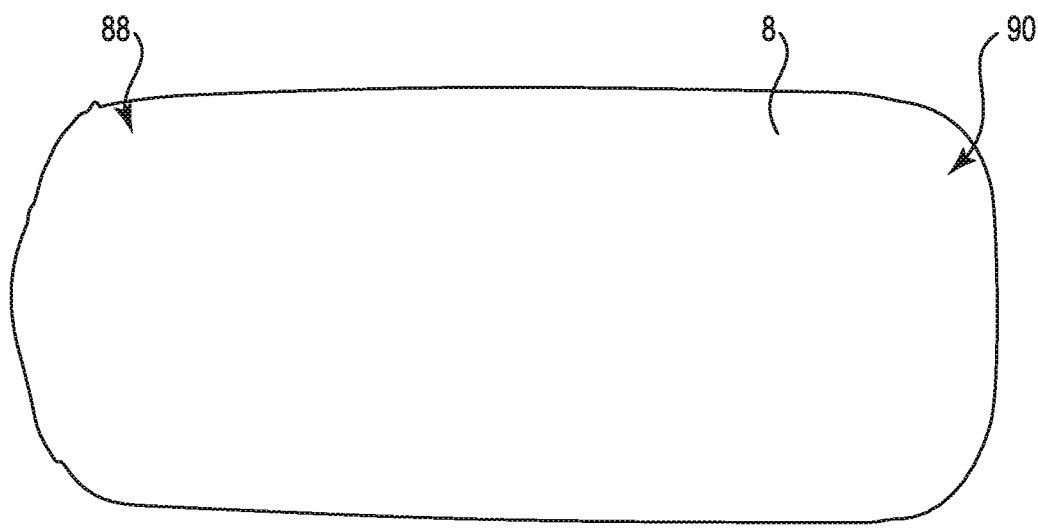
FIG. 11 is an illustration of the elastic tube disposed about the fiber bundle, in accordance with embodiments described in the disclosure.

FIG. 11 is an illustration of the elastic tube 8 disposed about the fiber bundle 78, in accordance with embodiments described in the disclosure. The elastic tube 8 expands to fit around the fiber bundle 78 on the cylindrical shell 62. In some embodiments, the elastic tube 8 fits around at least a portion of one or both ends 88 and 90 of the fiber bundle 78, which can help to secure the elastic tube 8 on the fiber bundle 78.

Figure 12:
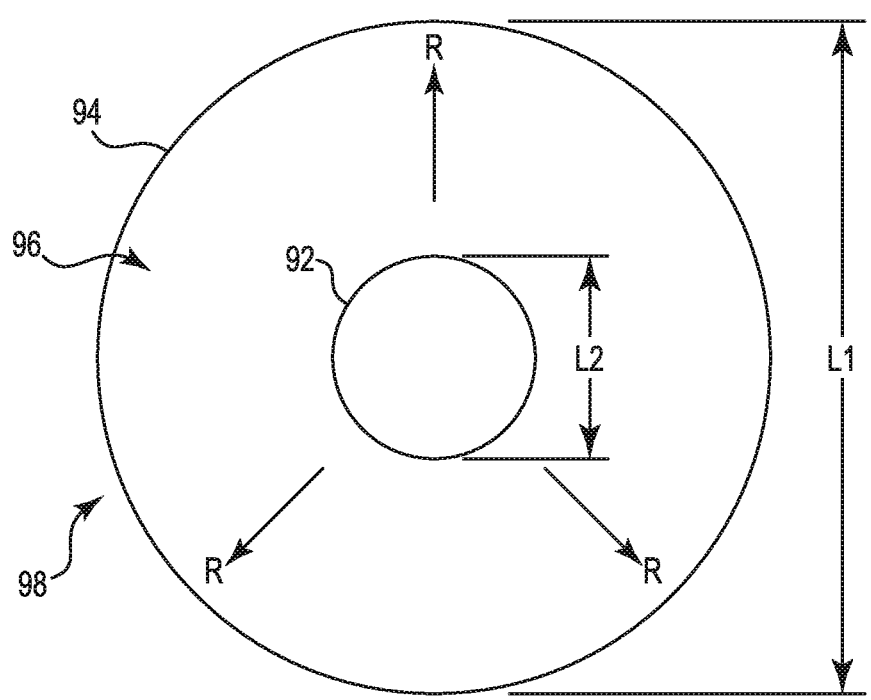
FIG. 12 is a cross-sectional illustration of the elastic tube showing the elastic tube in a non-expanded, relaxed condition, and in an expanded condition as disposed on the fiber bundle, in accordance with embodiments described in the disclosure.

FIG. 12 is a cross-sectional illustration of the elastic tube 8 showing the elastic tube 8 in a non-expanded, relaxed condition at 92, and in an expanded condition at 94 (as disposed on the fiber bundle 78), in accordance with embodiments described in the disclosure. The elastic tube 8 expands in the radial direction R to be disposed on the fiber bundle 78. In the expanded condition at 94, the elastic tube 8 has a diameter L1 and in the non-expanded, relaxed condition at 92, the elastic tube 8 has a diameter L2. In some embodiments, the ratio of the diameters L2/L1 is less than 0.5.

The elastic tube 8 has a tube interior 96 and a tube exterior 98. In the expanded condition at 94, when disposed on the fiber bundle 78 and situated in the blood processing apparatus 10, the fiber bundle 78 is situated next to the tube interior 96 and the housing 12 is situated next to the tube exterior 98.

Figure 13:
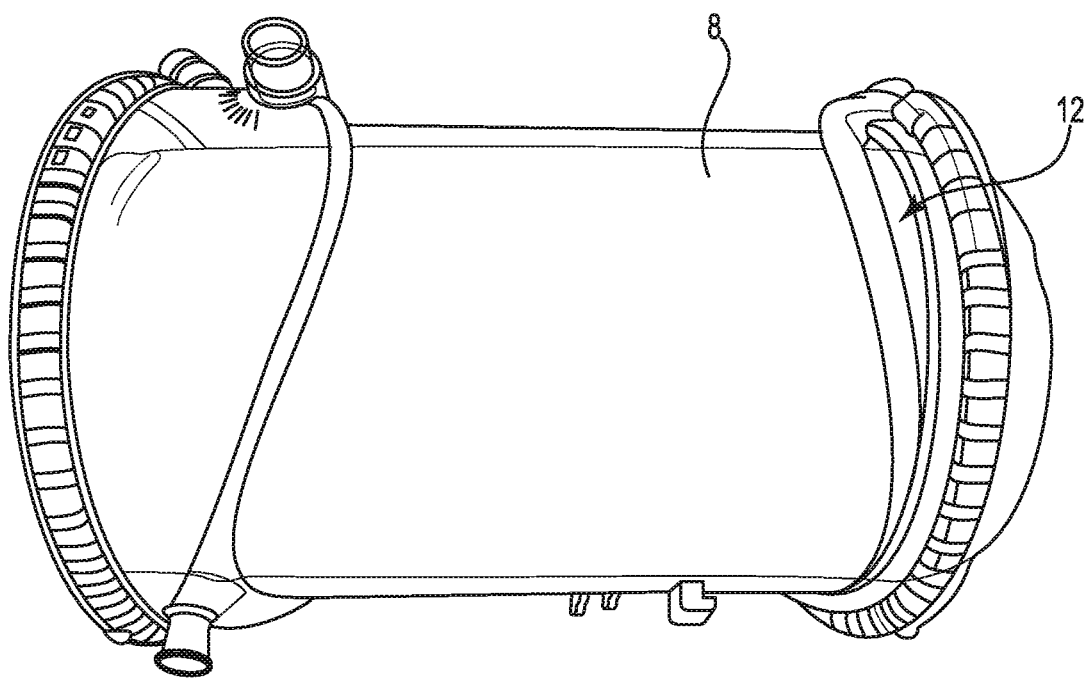
FIG. 13 is an illustration of the elastic tube disposed about the fiber bundle and introduced into the housing, in accordance with embodiments described in the disclosure.

FIG. 13 is an illustration of the elastic tube 8 disposed about the fiber bundle 78 and introduced into the housing 12, in accordance with embodiments described in the disclosure. As previously described, the elastic tube 8 is disposed about the gas exchanger element 76 to elastically constrain and protect the micro-porous hollow fibers of the fiber bundle 78. Also, the elastic tube 8 has a pore size that is large enough to permit blood to flow across the elastic tube 8, from the tube interior 96 to the tube exterior 98, without filtering micro-emboli from the blood and with a reduced hydraulic resistance to blood flow. The elastic tube 8 is not removed from the blood processing apparatus 10, such that the elastic tube 8 remains in the housing 12 during storage and operation of the blood processing apparatus 10. In some embodiments, the elastic tube 8 is situated about the fiber bundle 78 prior to insertion of the assembly, including the elastic tube 8, the fiber bundle 78, and the cylindrical shell 62, into the housing 12 of the blood processing apparatus 10.

Figure 14:
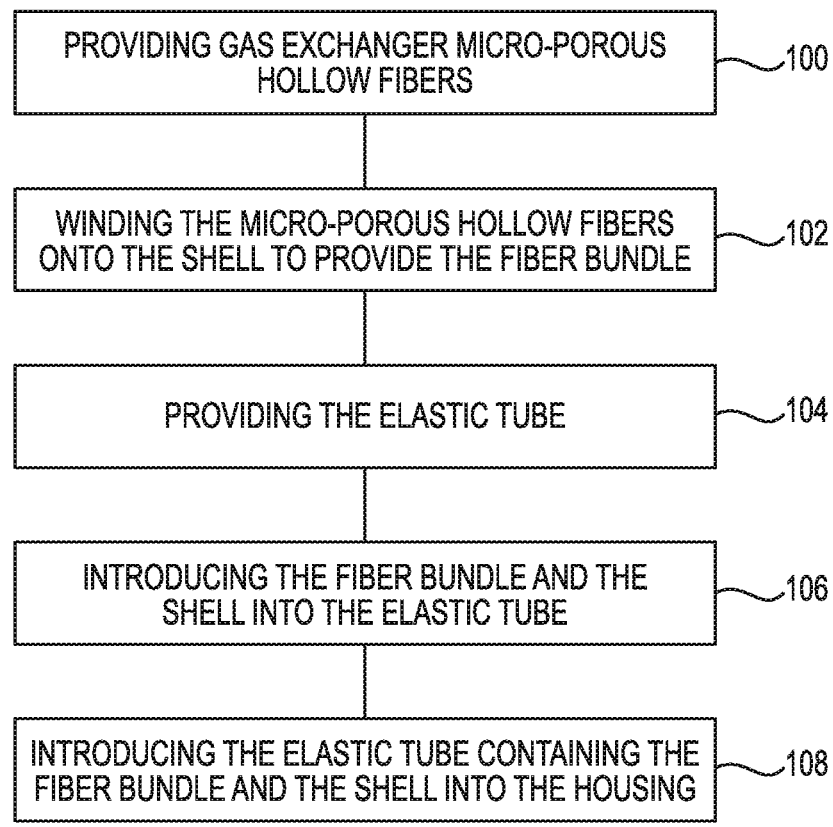
FIG. 14 is an illustration of a method of manufacturing the blood processing apparatus, in accordance with embodiments described in the disclosure.

FIG. 14 is an illustration of a method of manufacturing the blood processing apparatus 10, in accordance with embodiments described in the disclosure.

At 100, the method includes providing gas exchanger micro-porous hollow fibers. The gas exchanger 74 includes micro-porous hollow fibers that blood flows around and past for oxygenating the blood and removing carbon dioxide from the blood. In some embodiments, the micro-porous hollow fibers are made of plasma breakthrough resistant PMP hollow fibers. In other embodiments, the micro-porous hollow fibers are made of polypropylene, polyester, or another suitable polymer or plastic material.

At 102, the method includes winding the micro-porous hollow fibers onto the cylindrical shell 62 to provide the fiber bundle 78. The micro-porous hollow fibers are situated on and about the exterior surface of the cylindrical shell 62 to provide the fiber bundle 78 on the cylindrical shell 62. In some embodiments, the micro-porous hollow fibers are woven into fiber mats that are wound about the cylindrical shell 62 to provide the fiber bundle 78. In other embodiments, the shell 62 is not cylindrical, but another shape, such as cuboid shaped, triangular prism shaped, or hexagonal prism shaped.

At 104, the method includes providing the elastic tube 8 including the fiber web 82 that permits blood to flow across the fiber web 82 without filtering micro-emboli from the blood. In some embodiments, providing the elastic tube 8 includes knitting an elastomeric yarn to provide the elastic tube 8. In some embodiments, providing the elastic tube 8 includes knitting an elastomeric yarn to provide the elastic tube 8 using a circular machine.

At 106, the method includes introducing the fiber bundle 78 and the cylindrical shell 62 into the elastic tube 8. The elastic tube 8 elastically constrains and protects the micro-porous hollow fibers of the fiber bundle 78. Also, the elastic tube 8 has a pore size that is large enough to permit blood to flow across the elastic tube 8, from the tube interior 92 to the tube exterior 94, without filtering micro-emboli from the blood and with a reduced hydraulic resistance to blood flow.

At 108, the method includes introducing the elastic tube 8 containing the fiber bundle 78 and the cylindrical shell 62 into the housing 12, such that the fiber web 82 elastically constrains the gas exchanger hollow fibers and protects the gas exchanger hollow fibers from being damaged by the housing 12. The elastic tube 8 is not removed from the blood processing apparatus 10, such that the elastic tube 8 remains in the housing 12 during storage and operation of the blood processing apparatus 10.

Figure 15:
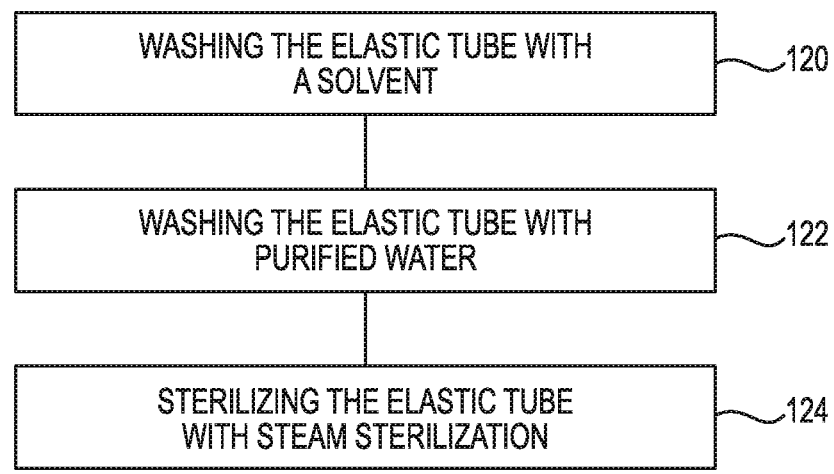
FIG. 15 is an illustration of a method of pre-cleaning the elastic tube used in the blood processing apparatus, in accordance with embodiments described in the disclosure.

FIG. 15 is an illustration of a method of cleaning the elastic tube 8 prior to assembling the blood processing apparatus 10, in accordance with embodiments described in the disclosure. The method includes, washing the elastic tube 8 with a solvent at 120, washing the elastic tube 8 with purified water at 122, and sterilizing the elastic tube 8 with steam sterilization at 124. Then the elastic tube 8 can be used in the blood processing apparatus 10.

Various modifications and additions can be made to the exemplary embodiments discussed without departing from the scope of the present disclosure. For example, while the embodiments described above refer to particular features, the scope of the disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood processing apparatus comprising:
a housing having a blood inlet and a blood outlet;
a shell situated in the housing and configured to receive blood through the blood inlet and including a surface and one or more apertures extending through the surface to permit the blood to flow to an exterior of the shell;
a fiber bundle including gas exchanger hollow fibers situated about the shell such that gas flows through the gas exchanger hollow fibers and the blood flows across the gas exchanger hollow fibers; and
an elastic tube including a fiber web situated about the fiber bundle and configured to elastically constrain and protect the gas exchanger hollow fibers during insertion into the housing, the fiber web having an average pore size diameter with a best fit circle in a range of from 150 to 800 micrometers such that the fiber web permits the blood to flow across the fiber web without filtering micro-emboli from the blood, wherein a ratio (L2/L1) of a diameter of the elastic tube in an unexpanded state (L2) to a diameter of the elastic tube in an expanded state (L1) disposed on the fiber bundle is less than 0.5.

2. The blood processing apparatus of claim 1, wherein the fiber web has an average pore size diameter with a best fit circle of 350 micrometers.

3. The blood processing apparatus of claim 1, wherein the fiber web has an average pore size diameter with a best fit circle in a range of from 200 to 500 micrometers.

4. The blood processing apparatus of claim 1, wherein the fiber web has an average pore size diameter with a best fit circle of greater than 200 micrometers.

5. The blood processing apparatus of claim 1, wherein the fiber web permits the blood to flow across the fiber web without filtering solid and gaseous micro-emboli of less than 120 micrometers in diameter of a best fit circle.

6. The blood processing apparatus of claim 1, wherein the fiber web permits the blood to flow across the fiber web without filtering solid and gaseous micro-emboli including blood clots and bubbles.

7. The blood processing apparatus of claim 1, wherein the fiber web permits the blood to flow across the fiber web without filtering solid and gaseous micro-emboli otherwise captured by average pore sizes of between 20 and 120 micrometers.

8. The blood processing apparatus of claim 1, wherein the elastic tube includes an elastomeric yarn.

9. The blood processing apparatus of claim 1, wherein the elastic tube includes a knit weave of elastomeric yarn.

10. The blood processing apparatus of claim 1, wherein the elastic tube includes an elastomeric yarn that includes an inner core of polyurethane elastic fiber covered with a nylon yarn.

11. The blood processing apparatus of claim 1, wherein the fiber web includes a coating of a wetting agent to decrease contact angles of surfaces and improve wettability.

12. The blood processing apparatus of claim 1, wherein the elastic tube extends at least partially around at least one end of the fiber bundle.

13. A blood processing apparatus comprising:
a housing having a blood inlet and a blood outlet;
a heat exchanger situated in the housing and configured to receive blood through the blood inlet and regulate the temperature of the blood;
a shell situated about the heat exchanger and including a surface and one or more apertures extending through the surface to permit the blood to flow to an exterior of the shell;
a fiber bundle including gas exchanger hollow fibers situated about the shell such that gas flows through the gas exchanger hollow fibers and the blood flows across the gas exchanger hollow fibers; and
an elastic tube having a tube interior and a tube exterior such that the fiber bundle is situated in the tube interior and the tube exterior is situated next to the housing and the elastic tube elastically constrains and protects the gas exchanger hollow fibers as the fiber bundle and the elastic tube are introduced into the housing and maintained in the housing, wherein the elastic tube has an average pore size diameter with a best fit circle in a range from 150 to 800 micrometers that permits the blood to flow from the tube interior to the tube exterior without filtering micro-emboli from the blood and with a reduced hydraulic resistance to blood flow, wherein a ratio (L2/L1) of a diameter of the elastic tube in an unexpanded state (L2) to a diameter of the elastic tube in an expanded state (L1) disposed on the fiber bundle is less than 0.5.

14. The blood processing apparatus of claim 13, wherein the elastic tube has an average pore size diameter with a best fit circle of 350 micrometers to provide a reduced hydraulic resistance to blood flow.

15. The blood processing apparatus of claim 13, wherein the elastic tube has an average pore size diameter with a best fit circle of 500 micrometers or less to provide a reduced hydraulic resistance to blood flow.

16. The blood processing apparatus of claim 13, wherein the elastic tube permits the blood to flow from the tube interior to the tube exterior without filtering solid and gaseous micro-emboli otherwise captured by average pore sizes of between 20 and 120 micrometers.

17. The blood processing apparatus of claim 13, wherein the elastic tube permits the blood to flow from the tube interior to the tube exterior without filtering solid and gaseous micro-emboli including blood clots and bubbles.

18. The blood processing apparatus of claim 13, wherein the gas exchanger hollow fibers include plasma resistant polymethylpentene (PMP) hollow fibers.

19. A method of manufacturing a blood processing apparatus comprising:
providing gas exchanger hollow fibers;
winding the gas exchanger hollow fibers onto a shell to provide a fiber bundle on the shell;
providing an elastic tube including a fiber web having an average pore size diameter with a best fit circle in a range of from 150 to 800 micrometers that permits blood to flow across the fiber web without filtering micro-emboli from the blood, wherein a ratio (L2/L1) of a diameter of the elastic tube in an unexpanded state (L2) to a diameter of the elastic tube in an expanded state (L1) disposed on the fiber bundle is less than 0.5;
introducing the fiber bundle and the shell into the elastic tube; and
introducing the elastic tube containing the fiber bundle and the shell into a housing such that the fiber web elastically constrains the gas exchanger hollow fibers and protects the gas exchanger hollow fibers from being mechanically damaged by the housing.

20. The method of claim 19, comprising maintaining the elastic tube in the housing prior to and during use of the blood processing apparatus.

21. The method of claim 19, wherein providing gas exchanger hollow fibers and winding the gas exchanger hollow fibers onto a shell comprises:
providing plasma resistant polymethylpentene (PMP) hollow fibers; and
winding the plasma resistant polymethylpentene (PMP) hollow fibers onto the shell.

22. The method of claim 19, wherein providing an elastic tube comprises:
knitting an elastomeric yarn to provide the elastic tube.

23. The method of claim 19, wherein providing an elastic tube comprises:
knitting an elastomeric yarn to provide the elastic tube using a circular machine.

* * * * *